(12) United States Patent
Gordon et al.

(10) Patent No.: US 7,045,676 B1
(45) Date of Patent: *May 16, 2006

(54) TRANSGENIC ANIMALS SECRETING PROTEINS INTO MILK

(75) Inventors: Katherine Gordon, Boston, MA (US); Suzanne Groet, Sudbury, MA (US)

(73) Assignee: GTC Biotherapeutics, Inc., Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/938,322

(22) Filed: Aug. 31, 1992

Related U.S. Application Data

(60) Continuation of application No. 07/426,464, filed on Oct. 20, 1989, now abandoned, which is a continuation of application No. 07/109,922, filed on Oct. 19, 1987, now abandoned, which is a division of application No. 06/849,815, filed on Apr. 9, 1986, now abandoned.

(51) Int. Cl.
*A01K 67/00* (2006.01)
*C12P 21/00* (2006.01)
*C12N 15/00* (2006.01)

(52) U.S. Cl. .............................. 800/14; 800/7; 800/25
(58) Field of Classification Search ................ 800/7, 800/14, 25
See application file for complete search history.

(56) References Cited

U.S. PATENT DOCUMENTS 5,322,775 A * 6/1994 Clark et al. ................. 435/69.1
5,366,894 A * 11/1994 Clark et al.
5,476,995 A * 12/1995 Clark et al. ..................... 800/16

OTHER PUBLICATIONS

Yu-Lee et al (1986) Nucleic Acids Res. 14, 1883-1902.*
Campbell et al (1984) Nucleic Acids Res. 12, 8685-8697.*
Qasba et al (1984) Nature 308, 377-380.*
Jones et al (1985) J. Biolog. Chem. 260, 7042-7050.*
Yu-Lee et al (1983) J. Biol. Chem. 258, 10794-10804.*
Stewart et al (1984) Nucleic Acids Res. 12, 3895-3907.*
Kraemer et al "Gene Transfer into Pronuclei of Cattle and Sheep Zygotes".*
Hammer et al (1985) Nature 315, 680-683.*
Gordon et al (1987) Bio/Technology 5, 1183-1186.*
Gordon et al (1991) Bio/Technology 9, 835-838.*
Rosen et al., In Membrane Receptors and Cellular Regulation, Alan R. Liss, Inc., 1985 pp. 385-396.*
Jones et al., J. Biol. Chem. 360(11) : 7642-7650 (1985).*

* cited by examiner

*Primary Examiner*—Deborah Crouch
(74) *Attorney, Agent, or Firm*—Byron V. Olsen

(57) ABSTRACT

A DNA sequence containing a gene encoding a protein, the gene being under the transcriptional control in the DNA sequence of a mammalian milk protein promoter which does not naturally control the transcription of the gene, such DNA sequence including DNA enabling secretion of the protein.

41 Claims, 5 Drawing Sheets

TRANSGENIC ANIMALS SECRETING PROTEINS INTO MILK

This application is a continuation of Ser. No. 07/426,464 filed Oct. 20, 1989, now abandon which is a continuation of Ser. No. 07/109,922 filed Oct. 19, 1987, now abandon which is a division of Ser. No. 06/849,815 filed Apr. 9, 1986, now abandon.

BACKGROUND OF THE INVENTION

This invention relates to transgenic animals.

It is possible to insert foreign genes into vertebrate embryos, and for these genes to be incorporated into the genome of the resulting animal. Insertion of the foreign genes has been carried out mechanically (by microinjection), and with the aid of retrovirus vectors (for example, as is described in Huszar et al. (1985) P.N.A.S. U.S.A 82, 8587). The animals resulting from this process are termed "transgenic." The foreign genes can be sexually transmitted through subsequent generations and are frequently expressed in the animal. In some instances the proteins encoded by the foreign genes are expressed in specific tissues. For example, the metallothionein promoter has been used to direct the expression of the rat growth hormone gene in the liver tissue of transgenic mice (Palmiter et al., 1982 Nature 300:611). Another example is the elastase promoter, which has been shown to direct the expression of foreign genes in the pancreas (Ornitz et al., 1985 Nature 313:600). Developmental control of gene expression has also been achieved in transgenic animals, i.e., the foreign gene is transcribed only during a certain time period, and only in a particular tissue. For example, Magram et al. (1985, Nature 315:338) demonstrated developmental control of genes under the direction of a globin promoter; and Krumlauf et al. (1985, Mol. Cell. Biol. 5:1639) demonstrated similar results using the alpha-feto protein minigene.

SUMMARY OF THE INVENTION

In general, the invention features a DNA sequence containing a gene encoding a protein, the gene being under the transcriptional control of a mammalian milk protein promoter which does not naturally control the transcription of the gene, the DNA sequence further including DNA enabling secretion of the protein; e.g., a secretion signal-encoding sequence interposed between the gene and promoter. The promoter can be that of a milk serum protein or a casein protein, although milk serum proteins are preferred, as will be discussed in more detail below. (As used herein, "gene" refers to both genomic DNA sequences and cDNA sequences.)

The invention permits the production of any desired protein in an easily maintained stable, portable culture system, i.e., a living domesticated mammal, which is capable not only of producing the desired protein, but preferably of passing on the ability to do so to its female offspring as well. Secretion of the protein into the host mammal's milk facilitates purification and obviates removal of blood products and culture media additives, some of which can be toxic or carcinogenic. More importantly, protein yields will be high and production will be more cost effective and efficient.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

DNA SEQUENCE ELEMENTS

Promoter

Figure 1:
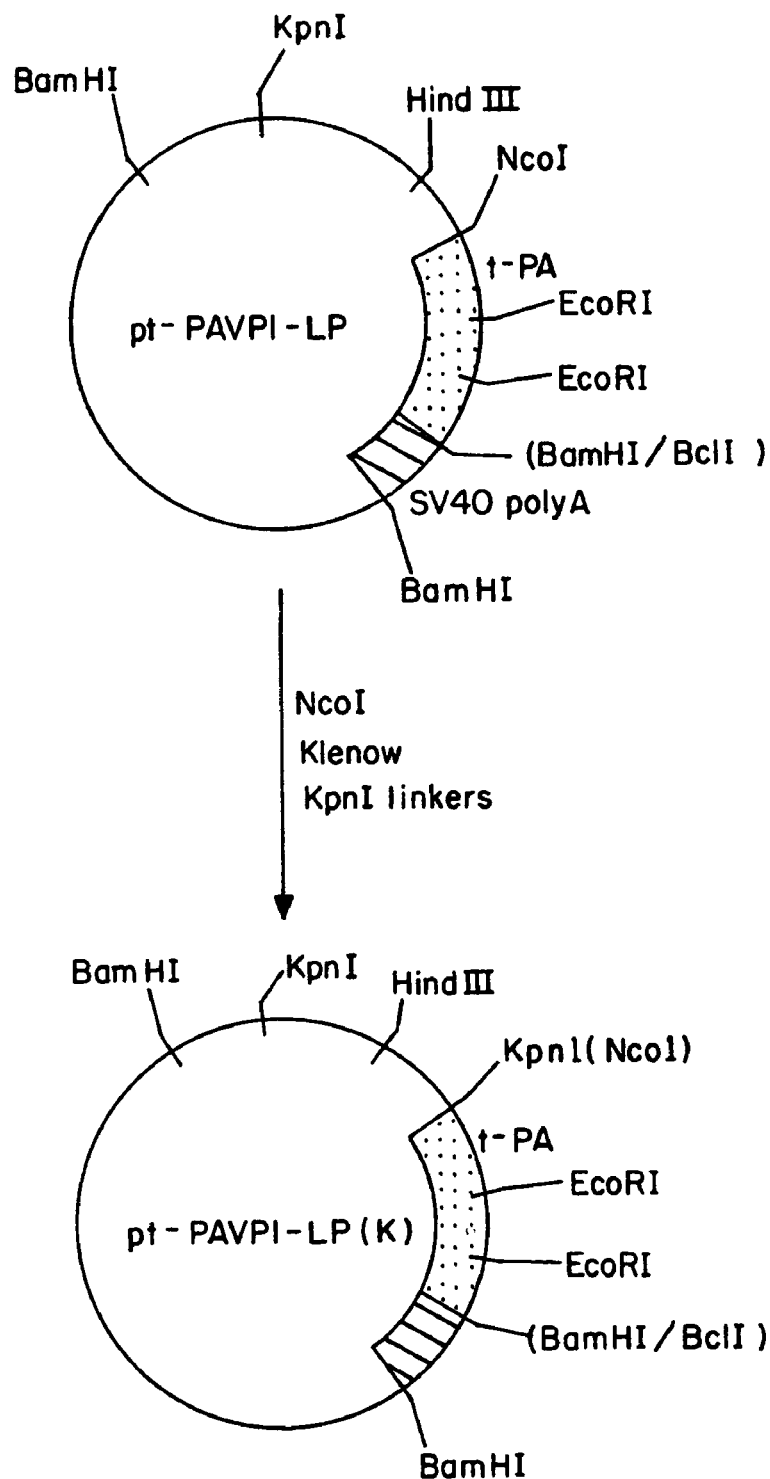
FIG. 1 is a diagrammatic representation of the construction of an intermediate vector of the invention, pt-PA VP1-LP(K).

The milk protein promoter can be derived from any mammalian species, and can be any promoter naturally associated with any protein which is normally secreted into mammalian milk. Generally, milk proteins are classified as the caseins, which are defined herein as the milk proteins which are present in milk in the form of micelles, and which are removed from skim milk by clotting with rennet; and the milk serum proteins, which are defined herein as the non-casein milk proteins. Whey proteins constitute the predominant fraction of the milk serum proteins, and in rodents include the protein known as whey acid protein. Whey acid protein ("WAP") is named based on its acidic isoelectric point (Piletz (1981) J. Biol. Chem. 256: 11509). Another example of a milk serum protein described in the literature is α-lactalbumin (described, along with mouse WAP, in Hennighausen and Sippel (1982) Eur. J. Biochem. 125, 131). Milk proteins are discussed in detail in Walstra and Jenness *Dairy Chemistry and Physics* (John Wiley & Sons 1984).

Generally, milk serum protein promoters are preferable to casein promoters in the present invention because caseins generally are produced in female mammals during pregnancy as well as after birth, while WAP is expressed primarily during post-partum lactation. This difference is of potential importance for two reasons. First, pre-birth production of the desired protein under the transcriptional control of a casein promoter could be wasteful, since the protein cannot be isolated from milk until it is secreted into the milk post-partum. Second, where the desired protein is toxic in large amounts (human tissue plasminogen activator (t-PA) is an example), a build-up of the protein in the tissues prior to lactation could be deleterious to the health of the host mammal. An additional advantage of some whey promoters such as the WAP promoter is that they are strong promoters, as evidenced by the large amounts of some whey proteins present in milk. Casein promoters also have this advantage.

Milk protein genes from which promoters, in addition to the WAP promoters, can be isolated, can be obtained in the same manner in which the WAP genes were isolated, as described in Hennighausen and Sippel, id, and Campbell et al. (1984) Nucleic Acids Research 12, 8685. The method generally involves isolating the mRNA from a lactating mammary gland, constructing a cDNA library from the mRNA, screening the library for the particular milk protein cDNA being sought, cloning that cDNA into vectors, and using the appropriate cDNA as a probe to isolate the genomic clone from a genomic library. A sequence upstream from the transcription start site in the genomic clone constitutes a putative "promoter", a genomic sequence preceeding the gene of interest and presumed to be involved in its regulation. The promoter may be isolated by carrying out restriction endonuclease digestions and subcloning steps. Promoters need not be of any particular length nor to have directly shown any properties of regulation. The mouse WAP promoter was isolated as a 2.6 kb EcoRI-Kpnl fragment immediately 5' to the WAP signal sequence.

Desired Protein

Any desired protein can be produced according to the invention. Preferred proteins are proteins useful in the treatment, prevention, and/or diagnosis of human disease; examples are t-PA and hepatitis B surface antigen. The invention is particularly useful for proteins which must be produced on a large scale to be economical, e.g., industrial enzymes and animal proteins.

Signal Sequence

It is necessary, for secretion of the desired protein into the milk of the host mammal, that the DNA sequence containing the gene for the desired protein include DNA which, when translated, causes the protein to be secreted out of the mammary tissue into the milk. Without such a sequence, the desired protein would remain in the mammary tissue, from which purification would be difficult, and would require sacrifice of the host animal. This DNA can encode a hydrophobic secretion signal which is cleaved during secretion. The signal sequence can be that which is naturally associated with the desired protein, if the protein is normally secreted (e.g., t-PA). Alternatively, the signal encoding sequence can be that of the milk protein providing the promoter, i.e., when the milk protein gene is digested and the promoter isolated, a DNA fragment is selected which includes both the promoter and the signal encoding sequence directly downstream from the promoter. Another alternative is to employ a signal encoding sequence derived from another secreted protein, which is neither the milk protein normally expressed from the promoter nor the desired protein.

Termination Site

Preferably there is located within or downstream from the 3' end of the desired gene a termination site. This site may be provided by sequences in the gene itself, or may need to be added. If the sequence is to be added, a preferred sequence is provided by the polyadenylation sequence of the virus SV40, as will be described in greater detail below.

Methods

Genetic Manipulations

Generally, all DNA manipulations used in the genetic constructions of the invention are carried out using conventional techniques, as described, e.g., in Maniatis et al. *Molecular Cloning: A Laboratory Manual* (Cold Spring Harbor Laboratory, 1982).

Introduction of DNA into Embryos

Once the genetic constructions have been produced in (vectors, e.g., plasmids, the promoter-signal sequence-desired protein-termination sequence DNA fragment is excised and then introduced into the desired mammalian embryo using, e.g., retroviruses or standard microinjection methods such as are described in Kraemer et al. (1985), Costantini and Jaenisch, eds., *Genetic Manipulaton of the Early Mammalian Embryo*, Cold Spring Harbor Laboratory (bovine embryo microinjection); Hammer et al. (1985) Nature 315, 680 (rabbit, sheep, and porcine embryo microinjection); and Gordon and Ruddle (1984) Methods in Embryology 101, 411 (mouse embryo microinjection). Micro-injection is preferably carried out on an embryo at the one-cell stage, to maximize both the chances that the injected DNA will be incorporated into all cells of the animal, including mammary tissue, and that the DNA will also be incorporated into the germ cells, so that the animal's offspring will be transgenic as well. Microinjection is a standard technique which involves, briefly, isolating fertilized ova, visualizing the pronucleus, and then injecting the DNA into the pronucleus by holding the ova with a blunt holding pipette of a diameter on the order of 50 μm, and using a sharply pointed pipette of a diameter on the order of 1.5 μm to inject buffer-containing DNA into the pronucleus. Following microinjection, the transgenic female animals are allowed to become sexually mature, mated, and milk collected post-partum.

Preferred host mammals are those which are already bred for large volume milk production, e.g., cows, sheep, goats, and pigs.

t-PA Production

There will now be described the construction of plasmid DNA in which the gene encoding human uterine t-PA, including the signal encoding sequence, is under the transcriptional control of the mouse WAP promoter, and has at its 3' end the SV40 polyadenylation site. This DNA was made from two intermediate plasmids, one carrying the mouse WAP promoter and one carrying the t-PA signal and structural sequences, as well as the SV40 polyadenylation site.

The WAP promoter containing plasmid pWAP-CAT (FIG. 2, obtained from Lothar Hennighausen, National Institutes of Health) was derived from a plasmid made according to the methods described in Hennighausen and Sippel (1982) Eur. J. Biochem. 125, 131; and Campbell et al. (1984) Nucleic Acids Research 12, 8685. In addition to containing the mouse WAP promoter, pWAP-CAT contains a gene which, for present purposes, is irrelevant: the CAT (chloramphenical acetyltransferase) gene, which does not form a part of the final DNA sequence which is microinjected.

Figure 2:
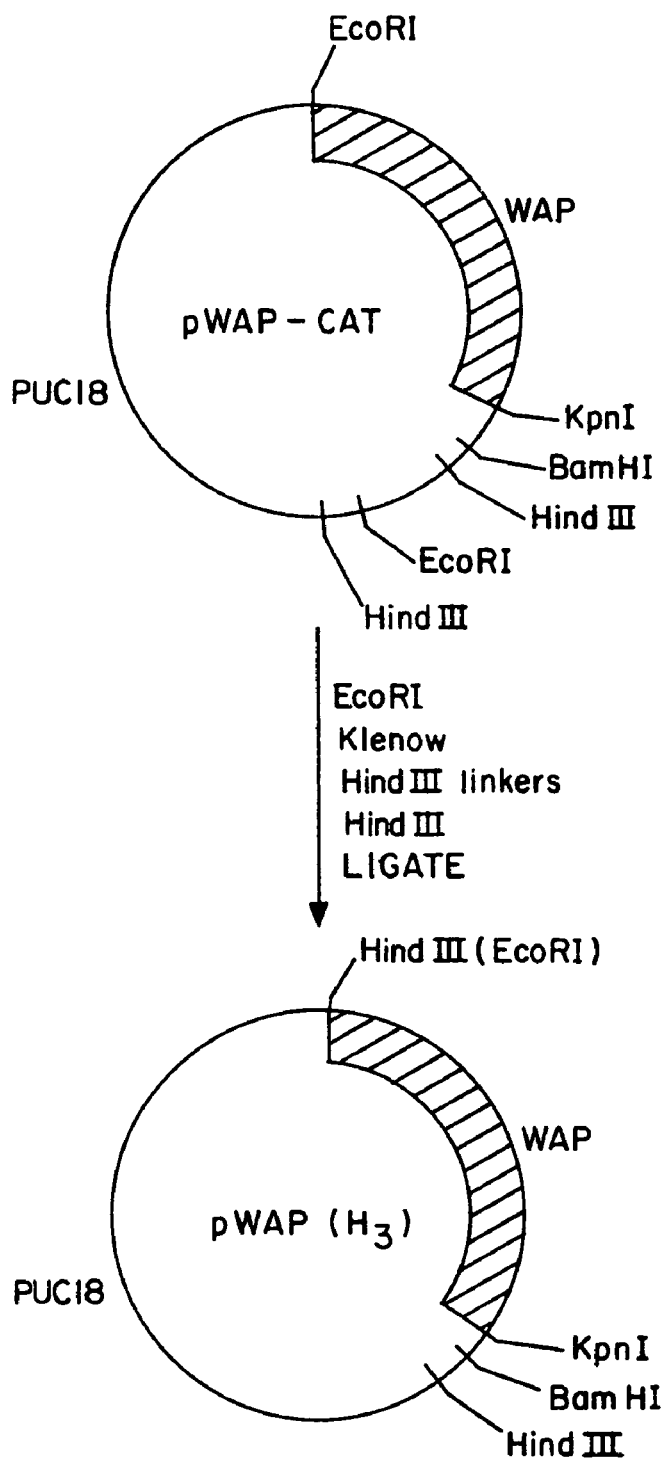
FIG. 2 is a diagrammatic representation of the construction of an intermediate vector of the invention, pWAP (H$_3$).

Still referring to FIG. 2, pWAP-CAT was modified to convert the EcoRI site to a HindIII site using Klenow and HindIII linkers.

The t-PA-containing plasmid pt-PA-VPI-LP(K) (FIG. 1) was derived from pt-PAVPI-LP, containing the t-PA gene (including the t-PA signal encoding sequence) and SV40 polyadenylation site, by modifying the unique NcoI site at the 5' end of the t-PA gene using NcoI endonuclease and Klenow and adding Kpn linkers to produce a KpnI site.

Figure 3:
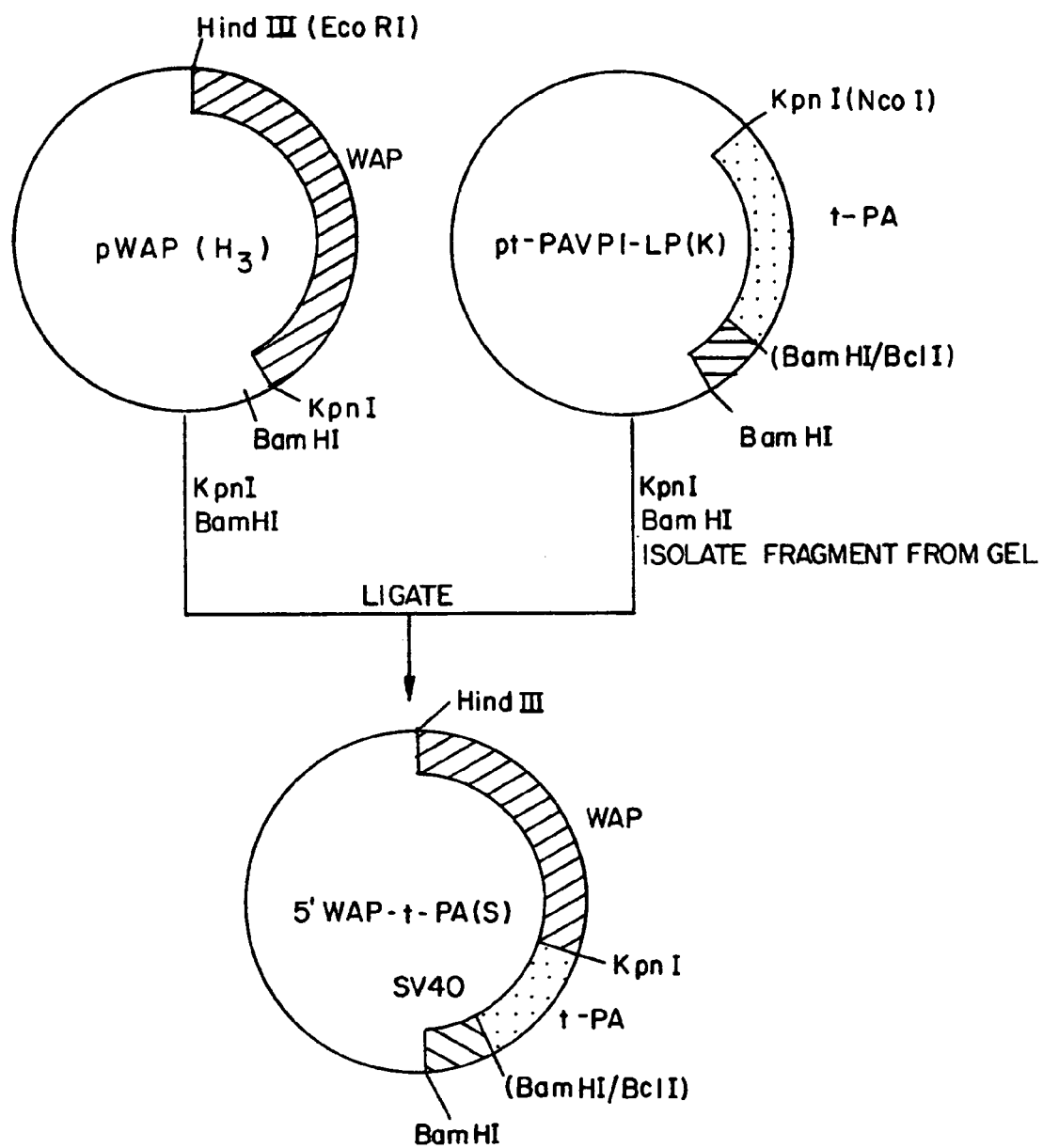
FIG. 3 is a diagrammatic representation of the construction of a vector of the invention, pWAP-t-PA(S).

Referring to FIG. 3, the KpnI-BamHI fragment of pt-PA VP1-LP(K), containing the t-PA gene and SV40 sequences, was isolated and ligated to BamHI-KpnI treated pWAP(H3) to form pWAP-tPA (S), which was then transformed into a TET-sensitive derivative of *E. coli* strain MC1061. This transformed strain, containing plasmid DNA in which the HindIII-BamHI fragment contains the t-PA gene including the t-PA signal encoding sequence under the transcriptional control of the WAP promoter and followed by the SV40 polyadenylation site, has been deposited in the American Type Culture Collection and given ATCC Accession No. 67032. Applicants' assignee, Integrated Genetics, Inc., acknowledges its responsibility to replace this culture should it die before the end of the term of a patent issued hereon, and its responsibility to notify the ATCC of the issuance of such a patent, at which time the deposit will be made available to the public. Until that time the deposit will be made available to the Commissioner of Patents under the terms of 37 CFR §1.14 and 35 USC §112. Assignee agrees that this designate culture will be maintained throughout the effective life of a patent granted, for 30 years from the date of deposit, or for 5 years after the last request for the deposit after issuance of the patent, whichever is longer.

Production of milk into which t-PA has been secreted is carried out by excising the HindIII-BamHI fragment from the deposited strain and transferring it by microinjection or other means preferably into the one-cell embryo of a mammal according to conventional methods, as described above. Alternatively, though less desirably, the entire plasmid or other restriction fragments can be introduced into the embryos. Embryos are then nurtured to term in vivo. Animals born from such manipulated embryos are screened for the presence of introduced DNA in the genome, and expression of t-PA in the milk is screened for among transgenic, lactating females. The protein from the milk of the adult lactating female animal will be assayed for t-PA by conventional procedures.

Production of Hepatitis B Surface Antigen

Figure 5:
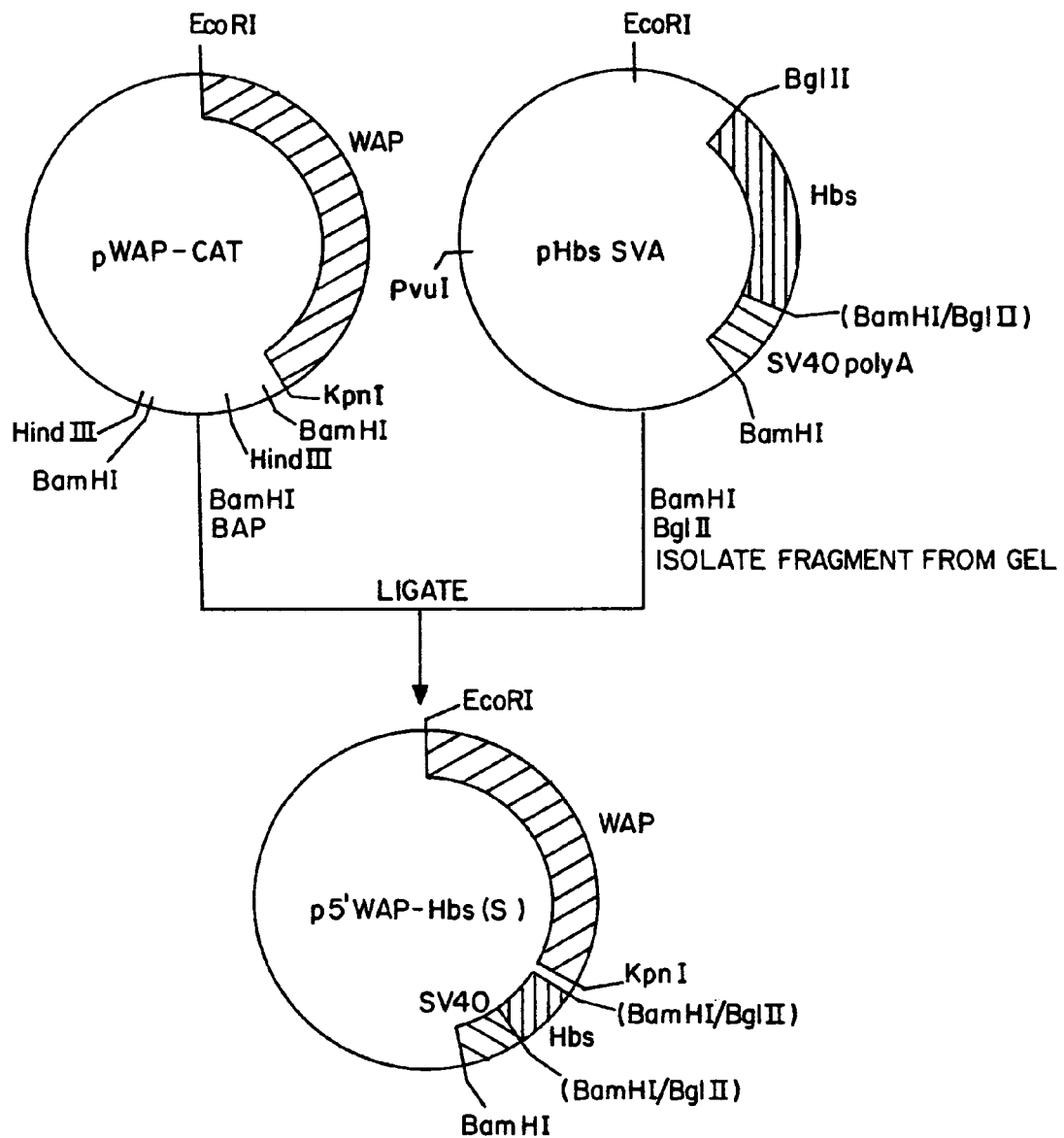
FIG. 5 is a diagrammatic representation of the construction of a vector of the invention, pWAP-Hbs(S).

Referring to FIG. 5, intermediate vectors pWAP-CAT and pHBsSVA were used to construct pWAP-Hbs(S), containing the gene for hepatitis B surface antigen, under the transcriptional control of the WAP promoter and followed by the SV40 polyadenylation site.

Figure 4:
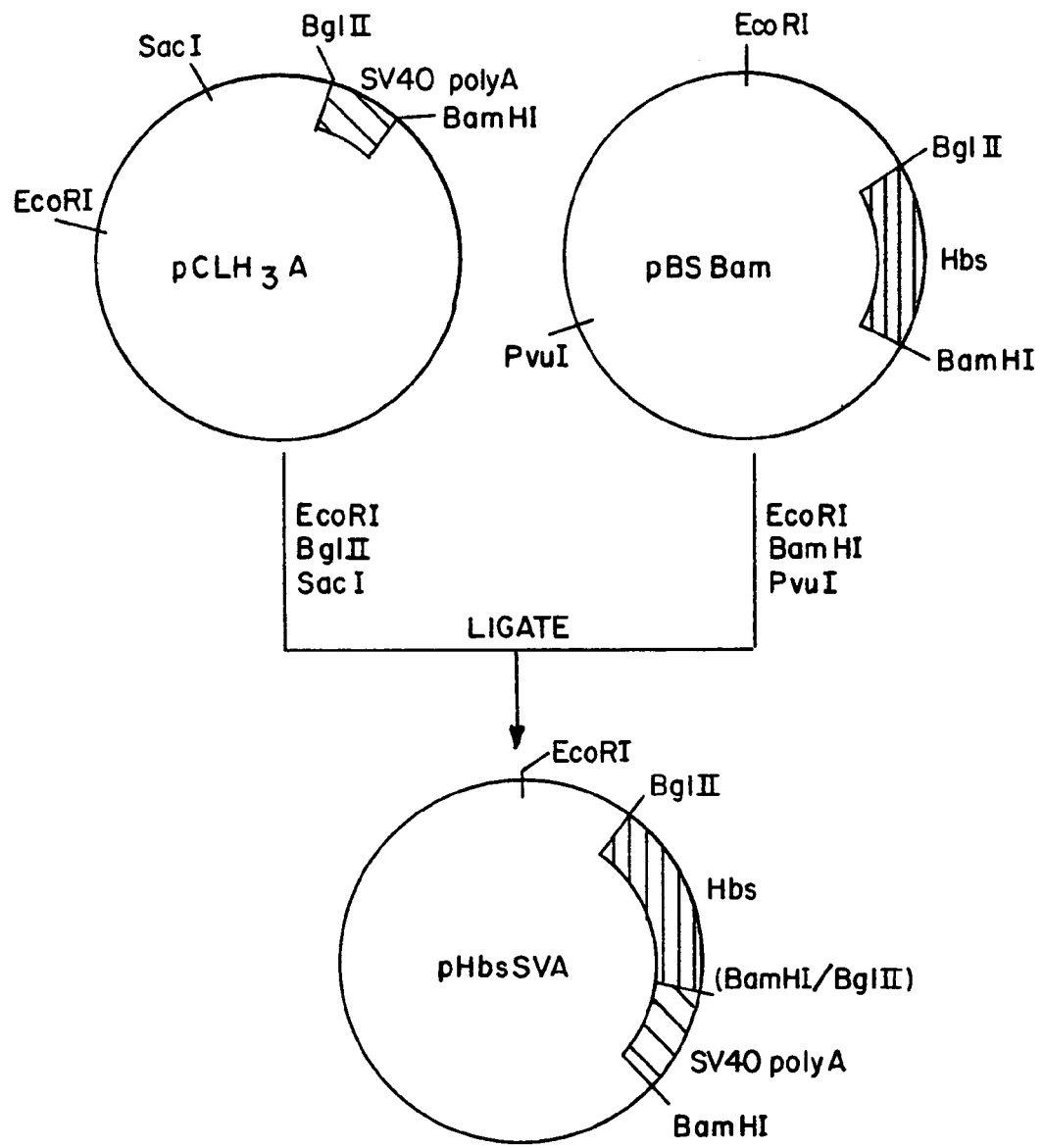
FIG. 4 is a diagrammatic representation of the construction of an intermediate vector of the invention, pHbsSVA.

The plasmid pWAP-CAT is described above. Plasmid pHbsSVA was constructed as illustrated in FIG. 4. pCLH$_3$A, containing the SV40 polyadenylation sequence, was restricted with EcoRI, SacI, and BglII. pBSBam, containing the gene for hepatitis B surface antigen, was cut with EcoRI, BamHI and PvuI, and the two mixtures ligated to give pHbsSVA, in which the SV40 sequence was positioned at the 3' end of the Hbs gene, on a BamHI-BglII fragment. This fragment was then ligated (FIG. 5) to BamHI and bacterial alkaline phosphatase-treated pWAP-CAT, transformed into E. coli strain MC1061, and the plasmid pWAP-Hbs(S) isolated.

The BamHI-EcoRI fragment of WAP-Hbs(S) can be excised and used as described above to produce hepatitis B surface antigen. Alternatively, though less desirably, the entire plasmid or other restriction fragments can be introduced into the embryos. Embryos are then nurtured to term in vivo. Animals born from such manipulated embryos are screened for the presence of introduced DNA in the genome, and expression of hepatitis B surface antigen in the milk is screened for among transgenic, lactating females. pWAP-Hbs(S) has been deposited in the American Type Culture Collection and given ATCC Accession No. 67033. Applicants' assignee, Integrated Genetics, Inc., acknowledges its responsibility to replace this culture should it die before the end of the term of a patent issued hereon, and its responsibility to notify the ATCC of the issuance of such a patent, at which time the deposit will be made available to the public. Until that time the deposit will be made available to the Commissioner of Patents under the terms of 37 CFR §1.14 and 35 USC §112. Assignee agrees that this designated culture will be maintained throughout the effective life of a patent granted, for 30 years from the date of deposit, or for 5 years after the last request for the deposit after issuance of the patent, whichever is longer.

Both pWAP-Hbs(S) and pWAP-t-PA(S) can be used as cassette vectors in which the hepatitis B surface antigen gene or the t-PA gene can be excised and replaced, using conventional methods, with any desired gene. If desired, the signal encoding sequence from pWAP-t-PA(S) can be left in the vector, and a gene lacking such a sequence inserted downstream of and in frame with it. Alternatively, the signal sequence from pWAP-t-PA(S) or pWAP-Hbs(S) can be removed along with the structural gene and the signal encoding sequence of the substituted gene employed. In addition, the WAP promoter alone can be excised and inserted into another desired expression vector.

Purification and Use

The proteins produced according to the invention are purified from the milk into which they have been secreted and used for their known purposes.

Hepatitis B surface antigen is useful in the production of hepatitis B vaccine, as described in Hsiung et al. U.S. Ser. No. 570,940, assigned to the same assignee as the present application, hereby incorporated by reference.

t-PA is useful in the treatment of thrombolytic disease in which fibrin clot lysis is necessary, as described in Wei et al. U.S. Ser. No. 782,686, assigned to the same assignee as the present application, hereby incorporated by reference. That patent application also describes general purification techniques which will be useful for milk-secreted proteins.

Stability in Milk

Table I below shows that, despite the presence in milk of numerous proteases, recombinant t-PA is stable when added to raw goat milk and incubated at 20° or 37° C. for 24 hours, with no evidence of loss of activity, as measured using the standard fibrin plate test (results not shown in Table I) or the amidolytic assay described in Wei et al., id. Similarly, recombinant hepatitis B surface antigen was found to be stable for at least 24 hours in raw goat milk (data not shown).

TABLE I

| | Amidolytic assay for TPA | | |
|---|---|---|---|
| | Incubation Time | Temperature | Units/ml |
| Goat milk alone | — | — | <20, <20 |
| Goat milk & TPA | 0 | — | 437, 368 |
| Goat milk & TPA | 24 hours | 20° C. | 419, 434 |
| Goat milk & TPA | 24 hours | 37° C. | 467, 507 |

OTHER EMBODIMENTS

Other embodiments are within the following claims. For example, other milk serum protein promoters can be used in place of the mouse WAP promoter, and the promoter can be derived from any mammalian species. For example, milk serum protein promoters such as that of β-lactoglobulin can be used, and the rat, rather than mouse, WAP promoter can be used; the rat WAP promoter is described in Campbell et al., id. Although less desirable than milk serum protein promoters, casein promoters can be used as well. The protein produced using the invention can be any desired protein of therapeutic or industrial importance.

The invention claimed is:

1. A method of producing a recombinant protein comprising the steps of:
    (a) inserting into an embryo of a nonhuman mammal a DNA construct comprising a gene encoding said protein, said gene being under transcriptional control of a milk protein promoter sequence that does not naturally control transcription of said gene, said DNA construct further comprising a DNA sequence encoding a signal peptide for enabling secretion of said protein into the milk of said mammal, (b) transferring the embryo to a female mammal of the same species, (c) allowing said embryo to develop into an adult nonhuman mammal whose genome comprises said DNA construct, (d) inducing lactation in said mammal or transgenic progeny of said mammal, wherein the progeny's genome comprises said DNA construct, (e) collecting milk from said lactating mammal or lactating progeny, and (f) isolating said protein from said collected milk.

2. The method of claim 1 wherein said protein is human tissue plasminogen activator.

3. The method of claim 1 wherein the signal peptide comprises a secretion signal sequence which is cleaved from said protein after secretion into said milk.

4. The method of claim 1 wherein the signal peptide is the secretion signal peptide naturally associated with said protein.

5. The method of claim 1 wherein the signal peptide is a secretion signal peptide naturally associated with a milk serum protein.

6. The method of claim 1 wherein said milk protein is a milk serum protein.

7. The method of claim 6, wherein said milk serum protein is α-lactalbumin.

8. The method of claim 1, wherein said gene is under the transcriptional control of a sequence upstream from the transcriptional start site of a mammalian milk protein which includes a milk protein promoter and which does not naturally control the transcription of said gene.

9. The method of claim 8, wherein said secretion-enabling DNA comprises a secretion signal-encoding sequence interposed between said gene and said promoter.

10. The method of claim 9, wherein said signal encoding sequence is the signal encoding sequence naturally associated with said gene encoding said protein.

11. The method of claim 9, wherein said signal encoding sequence is the signal encoding sequence naturally associated with said mammalian milk protein promoter.

12. The method of claim 8, wherein said milk protein is a milk serum protein.

13. The method of claim 12, wherein said milk serum protein is α-lactalbumin.

14. The method of claim 8, wherein said DNA sequence includes a transcriptional stop sequence.

15. The method of claim 14 wherein said stop sequence is a SV40 virus DNA sequence.

16. The method of claim 15 wherein said stop sequence is contained in the polyadneylation sequence of SV40.

17. A method of producing a recombinant protein comprising the steps of:

(a) providing an adult nonhuman mammal developed from an embryo of a nonhuman mammal, said embryo comprising a DNA construct comprising a gene encoding said protein, said gene being under transcriptional control of a milk protein promoter sequence that does not naturally control transcription of said gene, said DNA construct further comprising a DNA sequence encoding a signal peptide for enabling secretion of said protein into the milk of said mammal, wherein the genome of said mammal comprises said DNA construct, (b) inducing lactation in said mammal, (c) collecting milk from said lactating mammal, and (d) isolating said protein from said collected milk.

18. The method of claim 17, wherein said milk protein is a milk serum protein.

19. The method of claim 18, wherein said milk serum protein is α-lactalbumin.

20. The method of claim 17, wherein said gene is under the transcriptional control of a sequence upstream from the transcriptional start site of a mammalian milk protein which includes a milk protein promoter and which does not naturally control the transcription of said gene.

21. The method of claim 20, wherein said secretion-enabling DNA comprises a secretion signal-encoding sequence interposed between said gene and said promoter.

22. The method of claim 21, wherein said signal encoding sequence is the signal encoding sequence naturally associated with said gene encoding said protein.

23. The method of claim 21, wherein said signal encoding sequence is the signal encoding sequence naturally associated with said mammalian milk protein promoter.

24. The method of claim 20, wherein said milk protein is a milk serum protein.

25. The method of claim 24, wherein said milk serum protein is α-lactalbumin.

26. The method of claim 20, wherein said DNA sequence includes a transcriptional stop sequence.

27. The method of claim 26 wherein said stop sequence is derived from SV40 virus DNA.

28. The method of claim 27 wherein said stop sequence is contained in the polyadneylation sequence of SV40.

29. A method of producing a recombinant protein comprising the steps of:

(a) providing a lactating transgenic mammal whose genome comprises a DNA construct comprising a gene encoding said recombinant protein, said gene being under transcriptional control of a milk protein promoter sequence that does not naturally control transcription of said gene, said DNA construct further comprising a DNA sequence encoding a signal peptide for enabling secretion of said recombinant protein into the milk of said mammal, (b) collecting milk from said lactating mammal, and (c) isolating said recombinant protein from said collected milk.

30. The method of claim 29, wherein said recombinant protein is a human tissue plasminogen activator or a hepatitis B surface antigen.

31. The method of claim 29, wherein said milk protein is a milk serum protein.

32. The method of claim 31, wherein said milk serum protein is α-lactalbumin.

33. The method of claim 29, wherein said gene is under the transcriptional control of a sequence upstream from the transcriptional start site of a mammalian milk protein which includes a milk protein promoter and which does not naturally control the transcription of said gene.

34. The method of claim 33, wherein said secretion-enabling DNA comprises a secretion signal-encoding sequence interposed between said gene and said promoter.

35. The method of claim 34, wherein said signal encoding sequence is the signal encoding sequence naturally associated with said gene encoding said protein.

36. The method of claim 34, wherein said signal encoding sequence is the signal encoding sequence naturally associated with said mammalian milk protein promoter.

37. The method of claim 33, wherein said milk protein is a milk serum protein.

38. The method of claim 37, wherein said milk serum protein is α-lactalbumin.

39. The method of claim 33, wherein said DNA sequence includes a transcriptional stop sequence.

40. The method of claim 39, wherein said stop sequence is a SV40 virus DNA sequence.

41. The method of claim 40 wherein said stop sequence is contained in the polyadneylation sequence of SV40.

* * * * *

Disclaimer

7,045,676—Katherine Gordon, Boston, MA (US); Suzanne Groet, Sudbury, MA (US). TRANSGENIC ANIMALS SECRETING PROTEINS INTO MILK. Patent dated May 16, 2006. Disclaimer filed August 18, 2011, by the assignee, Genzyme Corporation.

The term of this patent shall not extend beyond the expiration date of Pat. No. 6,727,405.
*(Official Gazette September 20, 2011)*

UNITED STATES PATENT AND TRADEMARK OFFICE
CERTIFICATE OF CORRECTION

PATENT NO.         : 7,045,676 B1                                    Page 1 of 1
APPLICATION NO.    : 07/938322
DATED              : May 16, 2006
INVENTOR(S)        : Katherine Gordon et al.

It is certified that error appears in the above-identified patent and that said Letters Patent is hereby corrected as shown below:

On the title page item (73) should read:
        (73) Assignee: Genzyme Corporation
                         Boston, MA (US)

Signed and Sealed this
Eighth Day of November, 2011

David J. Kappos
*Director of the United States Patent and Trademark Office*